US00PP18226P3

(12) United States Plant Patent
Gargiulo

(10) Patent No.: US PP18,226 P3
(45) Date of Patent: Nov. 20, 2007

(54) GRAPEVINE '90-3437'

(50) Latin Name: *Vitis vinifera*
Varietal Denomination: 90-3437

(75) Inventor: Angel A. Gargiulo, San Rafael (AR)

(73) Assignee: M. Caratan, Inc., Delano, CA (US)

( * ) Notice: Subject to any disclaimer, the term of this patent is extended or adjusted under 35 U.S.C. 154(b) by 147 days.

(21) Appl. No.: 09/935,491

(22) Filed: Aug. 23, 2001

(65) Prior Publication Data

US 2006/0037117 P1 Feb. 16, 2006

(51) Int. Cl.
*A01H 5/00* (2006.01)

(52) U.S. Cl. ..... Plt./205; Plt./207

(58) Field of Classification Search ..... Plt./205, Plt./207

See application file for complete search history.

*Primary Examiner*—Kent Bell
(74) *Attorney, Agent, or Firm*—Jondle & Associates, P.C.

(57) ABSTRACT

A new and distinct cultivar of grapevine which is characterized by producing a large, bright purple to dark purple-skinned, seedless grape, is described.

1 Drawing Sheet

Genus and species: *Vitis vinifera.*
Variety denomination: '90-3437'.

BACKGROUND OF THE NEW VARIETY

The present invention relates to a new and distinct cultivar of grapevine referred to as grapevine '90-3437'. When treated with Gibberellic Acid, this variety produces seedless fruit which are mature for commercial harvesting and shipment approximately October 1 to October 15 in the San Joaquin Valley of central California.

The invention and development of new varieties of grapevines, as with other fruit producing varieties of plants, is a science marked by attentiveness, nurturing of the new varieties over lengthy periods of time, devotion to achieving the desired results and, in the end, good fortune. The variables associated with this process are countless and the results relative to the fruit produced, as to maturity date, size, quality, coloration, quantity and the like, may vary from growing season to growing season depending upon a multitude of influences. Variations in such influences may include, but are not limited to, seasonal variations such as temperature, rainfall, pests and diseases, as well as other factors which may be more reliably within control, such as the age of the plants, irrigation, pruning, fertilization, trellising practices and the like.

Nonetheless, such invention and development continues and superior varieties of grapevines are discovered and developed as a result of the arduous tasks required. More specifically, with respect to grapevines, there continues to be significant effort to develop new varieties which are superior in one or more respects over existing commercial varieties. Such respects include, for example, relative to the fruit, productivity, size, coloration, flavor, shipping quality, as well as other characteristics. Still another characteristic is the maturity period of the fruit of the new variety. It is frequently deemed desirable in a new variety that the fruit matures during a period of time in which no other desirable variety matures, or which is superior in other respects to varieties which may mature at approximately the same time.

The grapevine of the instant variety is a promising candidate for commercial success in respect to many of these criteria.

ORIGIN AND ASEXUAL REPRODUCTION OF THE NEW VARIETY

The present variety of grapevine was bred under the direction of the inventor in 1989 in Delano, Calif., by cross pollination between the female parent grapevine 'Red Globe' (unpatented) and the male parent grapevine '26916' (unpatented). A single plant was chosen from this hybridization and named '90-3437'. The present variety of grapevine was first asexually reproduced in 1990 in Delano, Calif. by grafting budwood of the new variety onto three-year old 'Salt Creek' woodstock. Subsequently, the resulting grapevines of the new variety were grown in the United States of America near Delano in the San Joaquin Valley of central California in a test plot. The observations and measurements hereof were made during the 1994 through 1999 growing seasons, at the same location near Delano in the San Joaquin Valley of central California. Grapevine '90-3437' has been found to retain its distinctive characteristics through successive asexual propagations.

SUMMARY OF THE NEW VARIETY

The new grapevine of the subject invention is characterized by its productivity producing large, seedless, light red-fleshed grapes which ripen for commercial harvesting and shipment approximately the same time as 'Emperor' (unpatented), or normally approximately October 1 to October 15 in the San Joaquin Valley of central California. The new variety may be compared in certain respects with 'Emperor'. Grapevine '90-3437' is a seedless grape, while grapevine 'Emperor' has a seeded grape. Additionally, grapevine '90-3437' produces larger berries and is darker in skin coloration than 'Emperor'.

Grapevine '90-3437' differs from the female grapevine parent 'Red Globe' (unpatented) in that grapevine '90-3437' has seedless grapes, while 'Red Globe' has seeded grapes.

Grapevine '90-3437' differs from the male grapevine parent '26916' (unpatented) in that grapevine '90-3437' has seedless light red-fleshed bright purple to dark purple-skinned grapes, while '26916' has white-fleshed and seeded grapes.

BRIEF DESCRIPTION OF THE DRAWING

The accompanying drawing is a color photograph of representative portions of the new grapevine of the present invention including bunches of grapes, sectioned portions of individual berries thereof, typical foliage and segments of canes.

DETAILED DESCRIPTION

The following descriptions have been observed under the ecological conditions prevailing near Delano in the San Joaquin Valley of central California. All major color code designations are by reference to the *Dictionary of Color,* by Maerz and Paul, First Edition, 1930 except for color references to the anthocyanin coloration of the immature tendrils and growing tips and the leaf mid-vein tinge, which employ the Munsell color charts for plant tissues by Kollmorgen Instruments Corporation, New Windsor, N.Y. Common color names are also occasionally employed.

GRAPEVINE

Generally:

*Size.*—The test grapevines of the subject variety are planted approximately 7.9 feet (240.79 cm) apart in the test rows and extend 11.8 feet (359.66 cm) apart. The grapevine canopy extends out into the row approximately 3.28 feet (99.97 cm). The canes of grapevine '90-3437' were trained to a maximum height of 38 inches. The grapevines are growing on their own roots and were four (4) years of age in 1999.

*Vigor.*—Very vigorous. The new variety is slightly more vigorous than 'Thompson Seedless' (unpatented) and about equal to 'Emperor'.

*Productivity.*—Very productive, slightly more productive than both the 'Thompson Seedless' and 'Emperor' grapevines. The test grapevines have been trained to a quadrilateral cordon production system.

Trunk:

*Size.*—Ranges from 6.5 cm (2.54inches) to 7.8 cm (3.04 inches) at 15 cm (5.85 inches) above ground surface.

*Surface texture.*—Course with a rough and somewhat shaggy surface.

*Bark color.*—Dark grey (15-A-6 Beaver Grey) to a lighter grey-brown (14-B-6 Camel's Hair).

Canes:

*Size.*—Thickness — Ranges from average to slightly above average depending upon the degree of light exposure and height in the grapevine canopy.

*Size.*—Diameter — Large vigorous canes range from 8 mm (0.32 inches) to 13 mm (0.52 inches). Length — The average cane length is 60 inches (5 feet).

*Surface texture.*—Mature cane is finely striated with low, fairly regular striations.

*Form.*—Woody shoot cross section form varies from circular to slightly elliptic.

*Color.*—One year or older wood — Ranges from a chamois tan (11-E-5 Raffia) to a darker tan-brown (13-D-7 Oakbuff).

*Internode.*—Length — Mature Cane — Normal.

*Internode.*—Length — Upper Mature Sun Cane — Ranges from 8 cm (3.12 inches) to 16 cm (6.24 inches) between nodes.

Tendrils:

*Size.*—Thickness — Medium.

*Size.*—Length — Mature Canes — Moderately long, ranging from 12 cm (4.68 inches) to 20 cm (7.8 inches). Diameter — 2.5 mm.

*Texture.*—Smooth.

*Distribution.*—Discontinuous.

*Form.*—Variable, most frequently trifid, but with numerous bifid forms present.

*Colors.*—Immature — Bronze-green (12-L-3 Pyrite Yellow) with a moderate amount of reddish (2.5R 6/8) anthocyanin pigmentation present.

Growing tips: The tip indument is moderately pubescent.

*Color.*—Expanding shoot tip is bright green-yellow (18-L-2 Citronelle) with a moderate amount of reddish (2.5R 6/8) anthocyanic pigmentation present.

LEAVES

Size — Generally — Large. Measurements have been taken from large mature leaves on vigorous canes.

*Average leaf blade length.*—Ranges from 14.6 cm (5.69 inches) to 17.5 cm (6.83 inches), measured from the petiole junction to the apex of the center leaf lobe.

*Color.*—Upwardly disposed surface — Ranges from a dark green (22-K-4) to a slightly darker green (23-C-6).

*Color.*—Downwardly disposed surface — Lighter grey-green (21-I-5) to a darker grey-green (21-H-6).

*Color.*—Leaf Vein — Lower mid-vein is prominent and pale green (17-G-4). The mid-vein is at times lightly tinged with a reddish-purple (2.5R 5/6) hue.

*Form.*—Mature leaves are most frequently pentagonal in shape with the largest leaves having from five to seven lobes. Apex — Acuminate. Base — Sagittate.

*Margin teeth.*—Sides — Most frequently convex in form with occasional straight-sided teeth present.

*Margin teeth.*—Length — Relatively large, ranging from 4 mm (0.16 inches) to 10 mm (0.4 inches).

*Surface.*—Relatively smooth.

*Petiolar sinus.*—Open with no basal lobe overlap. The petiolar sinuses are most frequently "U" shaped. The upper leaf sinuses are usually closed with moderate leaf overlap. The bases of the upper leaf sinuses are variable, most frequently "V" shaped, but at times "U" shaped bases can be present.

*Petiole.— Length — Varies from* 14.2 cm (5.54 inches) to 19.4 cm (7.57 inches).

*Petiole.*—Thickness — Ranges from 2.0 mm (0.08 inches) to 4.0 mm (0.16 inches), measured at mid-petiole.

*Petiole.*—Color — Ranges from a pale green (17-G-5) to a pale green-yellow (17-D-3).

*Petiole.*—Surface — Color — On mature leaves, the surface is often tinged with a purplish hue, most frequently at the distal end near the petiole juncture with the leaf blade base. This coloration can vary from a light rose (2-C-3) to a darker purple (4-J-3 Azalea).

FLORAL

Cluster:

*Generally.*—The floral cluster is moderately narrow and tapering. The first floral cluster can occur from the second to the fifth node, most frequently on node 3 or 4. The cluster frequency is high, imparting the potential for excellent productivity.

*Size.*—Length — Ranges from 11.5 cm (4.49 inches) to 17.5 cm (6.83 inches) without the peduncle.

*Size.*—Width — Ranges from 2.5 cm (0.975 inches) to 8.3 cm (3.24 inches).

*Peduncle.*—Length — Can vary from 2.5 cm (0.975 inches) to 4.0 cm (1.56 inches).

*Inflorescences.*—Hermaphroditic.

*Stamens.*—Upright.

*Anthers.*—Size — Average.

*Date of bloom.*—Full bloom in 1999 was May 31, approximately one week after 'Thompson Seedless'. The 1999 growing season can be characterized as a very late developing season, approximately ten (10) days later than an average year in Delano area in the San Joaquin valley of California. This would indicate a more "normal" or "average" date of bloom of May 21 for the new variety.

*Pollen.*—Abundant.

*Calyptra.*—Separation from the flower base is complete. The duration of bloom is normal, approximately ten (10) days.

*Calyptra.*—Color — Lighter green (19-K-4).

FRUIT

Maturity when described: Ripe for commercial harvesting and shipment in a normal growing season (approximately October 1 to October 15) near Delano in the central valley of California. The date of maturity is similar to that of the commercial variety 'Emperor'. The 1999 growing season was an unusually late year for maturity of most varieties and in which the maturity period of the new variety was approximately October 10 to October 25.

Cluster — primary bunches:

*Generally.*—Ranges from above medium to large.

*Bunch.*—Length — Ranges from 22 cm (8.58 inches) to 32 cm (12.48 inches) without the peduncle.

*Bunch.*—Width — Ranges from 15 cm (5.85 inches) to 21 cm (8.19 inches).

*Bunch.*—Density — Moderately loose with numerous visible pedicels.

*Berry.*—Number — Ranges from 85 to as many as 175 berries in the largest clusters.

*Bunch.*—Peduncle — Length — Ranges from 3.5 cm (1.365 inches) to 8.1 cm (3.159 inches).

*Bunch.*—Peduncle — Diameter — Ranges from 2.5 mm (0.1 inches) to 5.0 mm (0.2 inches).

*Peduncle.*—Color — Medium green-grown (14-K-1).

*Berry.*—Size — Large. Form — Lateral — Quite uniformly oval. Form — Cross-sectional — Globose. Uniformity — Good within the individual bunch. Brix content — 19.5 degrees. Size — Diameter — Ranges from 20 mm (0.8 inches) to 25 mm (1 inch). Size — Length — Ranges from 25 cm (1 inch) to 30 mm (1.2 inches).

*Berry.*—Color — Generally — Overall berry skin coloration is relatively uniform. Most exposed berries are 100% surface colored. The shaded side of interior berries can range from 70% to 100% colored.

*Skin.*—Color — Generally — All berry surfaces are covered with a very light greyish, waxy bloom.

*Skin.*—Color — Ranges from a bright purple-red (6-G-4) to a slightly darker (6-J-4).

*Ground.*—Color — Generally — Ranges from 5% to 30% of the surface on interior berries.

*Ground.*—Color — Usually a very pale yellow with a slight greenish tint (11-K-1). Often these ground color areas can have a very lightly blushed surface.

*Pedicel.*—Size — Medium.

*Pedicel.*—Length — Ranges from 8.0 mm (0.32 inches) to 13.0 mm (0.52 inches).

*Pedicel.*—Diameter — Ranges from 1.5 mm (0.06 inches) to 2.5 mm (0.1 inches) at mid-pedicel.

*Pedicel.*—Color — Greenish-brown (14-K-3 Serpentine Green).

*Pedicel.*—The berry attachment is very strong. Almost no shatter occurs at full maturity.

Secondary bunches: The secondary bunches are numerous. Berry shape is similar to the berries in the primary clusters. Berry size in the secondary clusters is smaller than that in the primaries. Color of the berries in the secondaries is darker than in the primaries and almost all berries are fully colored. Color ranges from a purple (6-J-5 Rubaiyat) to a darker (7-E-5 Mauverose). Secondary bunch form is irregular. Secondary bunches can range from 4 cm (1.56 inches) to 12 cm (4.68 inches) in width and from 7 cm (2.73 inches) to 14 cm (5.46 inches) in length. Berry counts vary substantially from just a few, six (6) to ten (10), up to thirty (30) berries or more.

Flesh:

*Flesh color.*—Variable, most frequently it is a combination of generally clear or translucent areas with colored areas. The translucent areas are often, but not always, near the stem end of the berry and the colored areas are often next to, or 2 mm (0.08 inches) to 4 mm (0.16 inches) under, the skin surface. The colored areas range from a light rose (3-E-2) to a darker rose (3-H-2).

*Juice.*—Color — Usually clear, but at times it can become slightly pink at advanced berry maturity.

*Juice production.*—Juicy.

*Flavor.*—Sweet and mild with excellent balance.

*Aroma.*—Bunch aroma is slight to lacking.

*Texture.*—Very good. The individual berries are crisp, firm and juicy.

*Seeds.*—Usually absent.

Use: High quality seedless table grape, well suited for commercial production.

Although the new variety of grapevine possesses the described characteristics noted above as a result of the growing conditions prevailing near in the central part of the San Joaquin Valley of California, it is to be understood that variations of the usual magnitude and characteristics incident to changes in growing conditions, irrigation, fertilization, pruning, pest control, climate variation and the like are to be expected.

I claim:

1. A new and distinct cultivar of grapevine plant as shown and described herein.

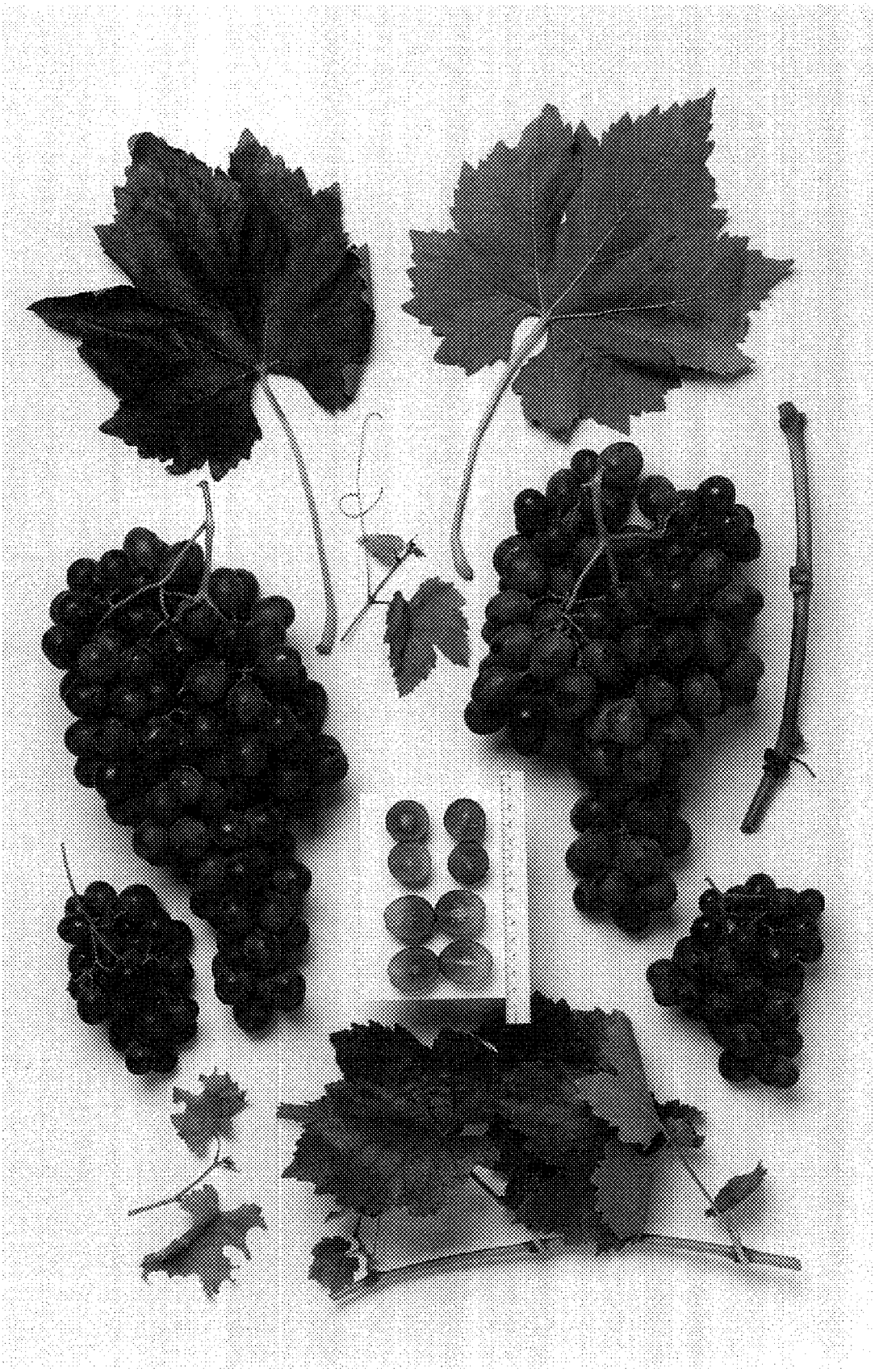

* * * * *